United States Patent [19]

Clausen et al.

[11] Patent Number: 6,048,708
[45] Date of Patent: Apr. 11, 2000

[54] PROCESS FOR PREPARATION OF β-LACTAMS AT CONSTANTLY HIGH CONCENTRATION OF REACTANTS

[75] Inventors: Kim Clausen, Tøløse, Denmark; Rocus M. Dekkers, Barendrecht, Netherlands

[73] Assignee: Gist-Brocades B.V., Netherlands

[21] Appl. No.: 08/776,115

[22] PCT Filed: Jul. 18, 1995

[86] PCT No.: PCT/EP95/02876

§ 371 Date: Feb. 19, 1997

§ 102(e) Date: Feb. 19, 1997

[87] PCT Pub. No.: WO96/02663

PCT Pub. Date: Feb. 1, 1996

[30] Foreign Application Priority Data

Jul. 18, 1994 [DK] Denmark ................................. 853/94

[51] Int. Cl.$^7$ ............................ C12P 37/04; C12N 11/10; C12N 9/84
[52] U.S. Cl. ............................ 435/45; 435/178; 435/230
[58] Field of Search ................................. 435/45, 43, 178, 435/230, 227, 252.1, 252.5, 252.8

[56] References Cited

U.S. PATENT DOCUMENTS 3,763,000 10/1973 Abe et al. ................................. 435/50
5,334,497 8/1994 Inaba et al. ................................. 435/3

FOREIGN PATENT DOCUMENTS

91/09136 6/1991 WIPO .
92/01061 1/1992 WIPO .

OTHER PUBLICATIONS

Mou "Biochemical Engineering and Beta–lactam Antibiotic Production" in Antibiotics Containing the Beta–lactam Structure. 1983 (Springer–Verlag:Berlin) p. 255–257.

*Primary Examiner*—Jon P. Weber
*Assistant Examiner*—Susan Hanley
*Attorney, Agent, or Firm*—Bierman, Muserlian and Lucas

[57] ABSTRACT

An improvement for enzymatically syhnthesizing a β-lactam compound is presented. The improvement comprises catalyzing the acylation of an amino β-lactam with an acylating agent for at least 5 hours with an amidase or acylase, wherein the concentration of each reactant is constantly higher than 70% of the lowest value of the saturated concentration of both reactants.

25 Claims, 1 Drawing Sheet

PROCESS FOR PREPARATION OF β-LACTAMS AT CONSTANTLY HIGH CONCENTRATION OF REACTANTS

This application is the National Stage of International Application No. PCT/EP95/02876, filed Jul. 18, 1995.

TECHNICAL FIELD

This invention relates to a an improved process for preparation of β-Lactam derivatives by enzymatic acylation of the parent amino β-lactam with an acylating agent.

BACKGROUND ART

Today, semisynthetic β-lactam derivatives such as ampicillin, amoxicillin, cefaclor, cephalexin, cephadroxil and cephaloglycin are, in an industrial scale, prepared by chemical methods, for example by reacting an amino β-lactam such as 6-aminopenicillanic acid, usually having its carboxyl group protected, with an activated side chain derivative, followed by the removal of the protecting group by hydrolysis. For example, ampicillin (6-D-α-aminophenylacetamido-penicillanic acid) can be prepared by reacting 6-APA, having a suitable protected carboxyl group, with D-phenylglycine acid chloride, followed by removal of the protecting group by hydrolysis. These reactions typically involve costly steps such as sub zero degree Celcius conditions and organic solvents like methylene chloride and silylation reagents.

Within the last years, there has been an increasing amount of publications concerning the possibility of enzymatic preparation of penicillins and cephalosporins by reaction of an acylating agent, be it in acid form or in activated form (for example, amide or ester) and the parent amino β-lactam (for example, 6-APA or 7-ADCA). For example, enzymatic production of ampicillin from 6-APA and a D-phenylglycine derivative (such as a lower alkyl ester) is known from West German patent application having publication No. 2,163,792, Austrian Patent No. 243,986, Dutch patent application No. 70-09138, West German patent application having publication No. 2,621,618, European patent application having publication No. 339,751 and PCT patent application having publication No. 92/01061.

The enzymatic acylation of an amino β-lactam with an acylating agent may be performed in the presence of a suitable amidase or acylase whereby the desired β-lactam derivative is formed. The parent amino β-lactam and the β-lactam derivative have the same β-lactam nucleus. In the β-lactam derivative endproduct the 6-$NH_2$ side chain of the penem parent β-lactam or the 7-$NH_2$ side chain of the cephem parent β-lactam are acylated.

This reaction can be illustrated by the following reaction scheme I:

Reaction Scheme I

Acylating agent+amino β-lactam→β-lactam derivative

If this process is performed batchwise, it has been discovered that at the beginning of the reaction, an increasing amount of β-lactam derivative is formed whereas, after a certain period of time, the amount of β-lactam derivative present in the reaction mixture is decreasing. The decomposition of the β-lactam derivative formed may be due to hydrolysis thereof whereby amino β-lactam and the acid form of the acylating agent is formed. In addition, the enzyme present may decompose the starting acylating agent. Consequently, at least two sorts of decomposition nay take place during such a reaction.

One object of this invention is to furnish a process whereby the molar ratio between the amount of β-lactam derivative which can be recovered from the reaction mixture and the acid form of the acylating agent formed during the reaction is increased, compared with this ratio for the known processes.

BRIEF STATEMENT OF THIS INVENTION

It has now, surprisingly, been found that improved process conditions are obtained if the enzymatic acylation of the amine β-lactam is performed at constantly high concentrations of both the parent amino β-lactam and the corresponding acylating agent. Preferably the concentrations of the parent amino β-lactam and of the corresponding acylating agent are higher than 70%, preferably higher than 85% of the lowest value of both the saturated concentration of the parent amino β-lactam and of the saturated concentration of the corresponding acylating agent.

The Advantages of this Invention are, Inter alia, as Follows

1) An improved molar ratio between the amount of β-lactam derivative which can be recovered from the reaction mixture and the amount of the acid form of the acylating agent, compared with this ratio for the known processes, is obtained. This improvement has direct impact on the economy of the process due to the reduced consumption of acylating agent versus β-lactam derivative which can be recovered from the reaction mixture. This improvement also has an indirect impact on the economy of the process due to the lower amount of the acid form of the acylating agent which is to be removed from the desired β-lactam derivative.
2) An increased yield of the β-lactam derivative is obtained.
3) An increase in the productivity of the β-lactam derivative is obtained. This productivity is defined as the amount of β-lactam derivative which can be recovered per time unit per volume unit of the reaction mixture.

DETAILED DESCRIPTION OF THIS INVENTION

Figure 1:
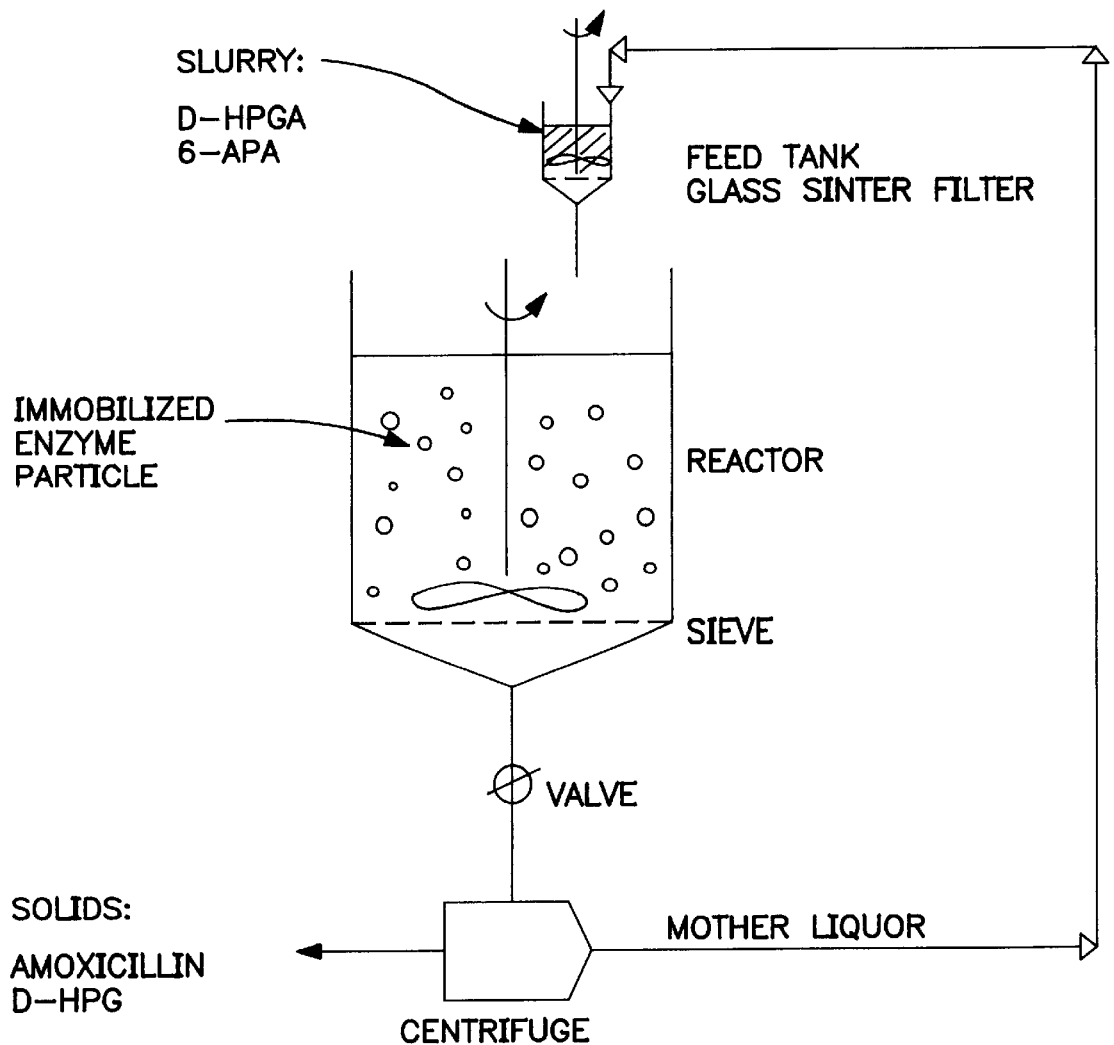
FIG. 1 is a picture of the equipment for the reaction.

Herein, the terms (parent) amino β-lactam and acylating agent have been used for the two starting materials. The term β-lactam derivative has been used for the desired end product.

As mentioned above, two undesired decomposition reactions take place during the process in question and these reactions have been illustrated in the following reaction scheme II which also shows the parent reaction from reaction scheme I:

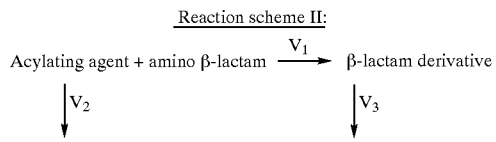

Reaction scheme II:

Acylating agent + amino β-lactam $\xrightarrow{V_1}$ β-lactam derivative $\downarrow V_2$       $\downarrow V_3$ -continued Acid form of the acylating agent  Acid form of the acylating agent
+
amino β-lactam In reaction scheme II, $v_1$ is the reaction rate for the reaction: acylating agent+amino β-lactam→β-lactam derivative, $v_2$ is the reaction rate for the reaction: acylating agent→acid form of the acylating agent, and $v_3$ is the reaction rate for the reaction: β-lactam derivative→acid form of the acylating agent+amino β-lactam.

One way of performing the process at constantly high concentrations of reactants according to this invention is to maintain the rate of formation of the desired β-lactam derivative in the reaction mixture ($v_1$) within a certain range for a certain period of time. Preferably, the rate of formation of the desired β-lactam derivative does, during a period of not less than 5 hours, preferably not less than 10 hours, not deviate more than ±50%, more preferred not more than ±20%, most preferred not more than ±10%, from the average rate of formation of the desired β-lactam derivative during the same period of time.

To take an example, if the average rate of formation of amoxicillin during a period of 20 hours is 2.6 μmoles/minute/ml reaction mixture, then the rate of formation of amoxicillin during this period of time should preferably be within the range from 1.3 to 3.9 μmoles/minute/ml.

Another way of performing the process at constantly high concentrations of reactants according to this invention is to maintain the net rate of formation of the desired β-lactam derivative in the reaction mixture ($v_1$ minus $v_3$) within a certain range for a certain period of time. Preferably, the net rate of formation of the desired β-lactam derivative does, during a period of not less than 5 hours, preferably not less than 10 hours, not deviate more than ±50%, more preferred not more than ±20%, most preferred not more than ±10%, from the average net rate of formation of the desired β-lactam derivative during the same period of time.

A still further way of performing the process at constantly high concentrations of reactants according to this invention is to maintain the ratio between, on one hand, the net rate of formation of the desired β-lactam derivative in the reaction mixture ($v_1-v_3$) and, on the other hand, the total rate of formation of the acid form of the acylating agent in the reaction mixture ($v_2+v_3$) within a certain range for a certain period of time. Hence, this ratio is $(v_1-v_3)/(v_2+v_3)$. Preferably, the ratio between the net rate of formation of the desired β-lactam derivative and the rate of formation of the acid form of the acylating agent does, during a period of not less than 5 hours, preferably not less than 10 hours, not deviate more than ±50%, more preferred not more than ±20%, most preferred not more than ±10%, from the average ratio between the net rate of formation of the desired β-lactam derivative and the rate of formation of the acid form of the acylating agent during the same period of time.

The β-lactam derivative formed may precipitate during the reaction and, also, the acid form of the acylating agent such as D-phenylglycine and D-p-hydroxyphenylglycine may precipitate. Hence, in some cases the reaction mixture will be a slurry throughout the reaction.

During the process of this invention, it is preferred that the total content of the desired β-lactam derivative, both in dissolved and optionally in precipitated form, in the reaction mixture is currently kept below a certain concentration. One object of doing so is to try to prevent that the viscosity of the reaction mixture becomes too high. Consequently, during the performance of the process at constantly high concentrations of reactants of this invention, it is preferred that the total content of the desired β-lactam derivative, both in dissolved and optionally in precipitated form, does not exceed 350 mM/liter reaction mixture and preferably does not exceed 250 mM/liter reaction mixture.

The process according to this invention may be performed in a reactor which is equipped with a device for stirring or mixing and with means for maintaining the reaction temperature within a certain range. Also, it is recommended that this reactor be connected with an equipment maintaining the pH value within a certain range.

During the continuous performance of the process, the amino β-lactam and the acylating agent may be added continuously or semicontinuously so as to maintain the desired concentrations thereof in the reaction mixture. The resulting β-lactam derivative and the acid form of the acylating agent may be removed continuously or semicontinuously from the reactor, for example, by removal, from the reactor, of a part of the reaction mixture from which the resulting β-lactam derivative and, possibly, the acid form of the acylating agent is removed, for example, by centrifugation or filtration. The mother liquor from this centrifugation or filtration may be returned to the reactor or may be used to dissolve the amino β-lactam or the acylating agent.

Herein, the semicontinuous performance of an action means that the action in question is performed several times within a certain period of time, for example, during an hour or during a day and night.

The (parent) amino β-lactam has a free amino group which is acylated by the reaction according to this invention. The amino β-lactam may conveniently be 6-APA, 7-ADCA, 7-ACA or 7-ACCC.

The amino β-lactam, for example 6-APA or 7-ADCA, used in the process of this invention may be obtained by enzymatic hydrolysis of the fermented penicillins or cephalosporins, (for example penicillin V, penicillin C or cephalosporin C) or their ring enlarged analogues (for example V-DCA and G-DCA) or derivatives thereof followed by removal of the hydrolysis by-product, if desired (phenoxyacetic acid etc.). Advantageously, the crude solution can be used directly without further purification or dilution.

The acylating agent may be in an activated form. Preferably, the acylating agent is an amide or an ester. The acylating agent may be a derivative of D-phenylglycine, D-p-hydroxyphenylglycine, D-2,5-dihydrophenylglycine or mandelic acid, such as a lower alkyl ester (methyl, ethyl, n-propyl or isopropyl ester) or an amide which is unsubstituted or substituted in the —$CONH_2$ group. The acylating agent may be used in the form of a salt, for example, the hydrochloride salt or the $H_2SO_4$ salt. The acylating agent may be added in an active form or the active form may be formed in situ.

The solubility of the acylating agent such as the D-phenylglycine or D-p-hydroxyphenylglycine derivative will vary with the identity of the derivative and with the composition of the reaction medium. In an aqueous system as used in the examples, the solubility of the hydrochloride salt of D-phenylglycine amide is typically approximately 450 mM. However, the solubility is very dependent on the salt components in the solution, as well as on the pH value and the temperature of the solution. As a further example, the solubility of the sulphate form of D-phenylglycin amide is about 3.3 M within a pH range from 2.5 to 6.5.

As appears from the above explanation, the acylating agent and the β-lactam derivative may be decomposed forming, inter alia, the acid form of the acylating agent. The acid form of the acylating agent is the parent carboxylic acid corresponding to the acylating agent in question.

Examples of β-lactam derivatives that may be prepared by the process of this invention are ampicillin, amoxicillin, cefaclor, cephalexin, cephadroxil, cephradine, epicillin and cefamandol.

The enzyme to be used in the process of this invention may be any enzyme catalyzing the reaction in question. Such enzymes have been known since around 1961. Enzymes to be used are, for example, termed penicillin amidase or penicillin acylase and classified as E.C. 3.5.1.11. A number of microbial enzymes are known to have this activity, derived from for example Acetobacter, Alcaligenes, Xanthomonas, Mycoplana, Protaminobacter, Aeromonas (West German patent application having publication No. 2,163,792) Pseudomonas (Austrian Patent No. 243986), Flavobacterium (Dutch patent application No. 70-09138), Aphanocladium, Cephalosporium (West German patent application having publication No. 2,621,618), *Acetobacter pasteurianum, Alcaligenes faecalis, Bacillus megaterium, Xanthomonas citrii* (European patent application having publication No. 339,751), *Kluyvera citrophila* (*Agr.Biol.Chem.* 37 (1973), 2797–2804) and *Escherichia coli* (West German patent application having publication No. 2,930,794). The *Escherichia coli* enzyme is commercially available. The enzyme also may be a so-called ampicillin hydrolase, acylase or amidase. In this connection, reference is, inter alia, made to *Hakko to Kogyo* 38 (1980), 216 et seg., the content of which is incorporated by reference.

It is preferred to use the enzyme in a reuseable form, for example, in entrapped or immobilized form. Immobilization may be done by any known method. Immobilized *Escherichia coli* enzyme is commercially available from Boehringer Mannheim GmbH, Germany, under the trade name Enzygel®, and Recordati under the trade name Super Enzyme®. Preferably, as enzyme Penicillin G acylase, immobilized on a carrier consisting of a gelling polycarbohydrate and a polymer containing free amino groups, is applied.

The process of this invention is generally carried out in a system containing water. If desired, an organic solvent may be added.

Generally, the reaction temperature of the process of this invention may vary between 0 and 35° C., especially between 10 and 30° C. Temperatures in the range from 20 to 30° C. may be preferred for convenient operation.

The suitable pH value depends, inter alia, on the type of the enzyme used. Using *Escherichia coli* enzyme, the pH value is typically in the range from 5 to 8, preferably in the range from 6.1 to 7. For the preparation of amoxicillin, a pH value in the range from 5.5 to 6.4 is preferred. Control of the pH value may be used.

Suitable reaction times are above 5 hours. The reaction time may be days or weeks.

Suitable enzyme concentrations may be from 1 to 100 U/ml (1 U=one unit of enzyme activity, see below).

Before the process is started, the reactor may be filled with the components in the desired amounts.

Using the process according to this invention, an extraordinary high molar ratio between the amount of β-lactam derivative which can be recovered and the total amount of acid form of the acylating agent can be obtained. These high ratios are obtained using the teachings of this invention and properly selecting the concentration of the acylating agent, the ratio between the concentration of acylating agent and the starting amino β-lactam, the pH value and the enzyme. Thus, a ratio of 2.4 was obtained in Example 1 below using the process according to the present invention. In a comparative batch process, vide Example 1 below, a molar ratio of only 1.4 was obtained. In addition, the yields of isolated product obtained in this example were 90 and 85%, respectively.

Purification of the product can be achieved by methods known per se, for example by crystallisation.

Herein, the following abbreviations have been used: 7-ACA is 7-aminocephalosporanic acid, 7-ACCC is 7-amino-3-chloro-3-cephem-4-carboxylate, 7-ADCA is 7-aminodesacetoxycephalosporanic acid, 6-APA is 6-aminopenicillanic acid, D-HPG is D-p-hydroxyphenylglycine, D-PG is D-phenylglycine, D-PC-A is D-phenylglycine amide, D-PGM is D-phenylglycine methyl ester, D-HPGM is D-p-hydroxyphenylglycine methyl ester, G-DCA is 7-phenylacetamidodesacetoxycephalosporanic acid, D-HPC-G is D-p-hydroxyphenylglycine amide, and V-DCA is 7-phenoxyacetamidodesazetoxycephalosporanic acid.

Any novel feature or combination of features described herein is material to this invention.

This invention is further illustrated by the following examples which, however, are not to be construed as limiting.

Definitions and Methods of Analysis

Enzyme

As enzyme Penicillin G acylase (26250 U, size 200–500 μm) isolated according to WO application 012782 immobilized on a carrier consisting of a gelling polycarbohydrate and a polymer containing free amino groups according to European patent 22642, is applied.

As definition of penicillin G acylase activity the following is used: one unit (U) corresponds to the amount of enzyme that hydrolyses per minute 1 μmole penicillin G under standard conditions (100 g.1$^{-1}$ Penicillin G potassium salt, 0.05 M potassium phosphate buffer, pH value 8.0, 28° C.).

HPLC Analysis of Ampicillin and Cephalexin

Column: RP LC-18, (250×4.6 mm; 5 μm)

Eluent A: 25 mM phosphate buffer, pH value 6.5

Eluent B: acetonitrile

| Gradient: Time, minutes | eluent B, % |
| --- | --- |
| 0→10 | 1→20 |
| 10→20 | 20 |
| Flow: 1 ml/min. | Detection: 215 nm. |

Retention times in minutes: 4.1 (D-PG); 6.3 (7-ADCA); 8.1 (6-APA); 9.1 (D-PGA); 13.4 (Cephalexin); 13.9 (Ampicillin); 18 (D-PGM).

HPLC Analysis of Amoxicillin

Column: Chromspher 018, 5 μm (100×3.0 mm)

Solvent: 25% acetonitrile in 12 mM phosphate buffer+ 0.2% sodiumdodecylsulphate, pH value: 2.6. Flow: 1 ml/min. UV-detection at 214 nm.

Retention times in minutes: 1.9 (D-p-hydroxyphenylglycine); 7.3 (D-HPGM); 3.1 (D-HPGA); 3.4 (6-APA); 4.8 (Amoxicillin).

EXAMPLE 1

Enzymatic Preparation of Amoxicillin from D-HPGM and 6-APA

The equipment for this experiment consisted of (see FIG. 1) a thermostated reactor having a volume of 1.5 liters, equipped with a three-bladed impeller and a sieve with slots 180 μm (open area about 32%) The reactor was connected to an autotitrator system using 4 M sulphuric acid as titrand. A valve was positioned at the outlet of the reactor. The outlet of the valve was connected via a pump to a basket centrifuge equipped with a polypropylene bag having a density of 1–5 μm. The outlet from the centrifuge was connected via a pump to a feed tank equipped with a stirrer and a glass sinter bottom. The outlet from the feed tank was connected via a pump to the reactor.

A mixture consisting D-HPGM (36.2 g, 200 mmol) and 6-APA (43.2 g, 200 mmol) in 800 ml water was added to the reactor with the bottom valve closed. The stirring was started. Immobilized Penicillin G acylase (26250 U, size 200–500 μm) made up to 200 ml was added to the reactor. The pH value was maintained at 6.1. The reaction temperature was about 20° C. Under these conditions, the reaction mixture was almost saturated with D-HPGM and 6-APA. Then, the bottom valve was opened allowing the reaction mixture from the reactor to enter the centrifuge. Thereafter, the mother liquor from the centrifuge was pumped into the feed tank wherein D-HPGM (21.7 g, 120 mmol) and 6-APA (20.0 g, 92.5 mmol) were loaded. The total volume of the suspension in the feed tank was kept at about 75 ml. A flow of about 100 ml/min was maintained in the system. The concentration of reaction components in the reactor, in the reactor outlet, in the centrifuge outlet, in the feed tank and in the feed tank outlet were monitored by analytical HPLC.

As the reaction proceeded, the amoxicillin and D-HPG formed started to precipitate out of solution. The crystals were separated from the immobilized enzyme particles by the bottom sieve in the reactor and the crystal suspension was led to the centrifuge where the crystals were separated from the mother liquor. When the mother liquor, which was now undersaturated with respect to D-HPGM and 6-APA, passed through the feed tank, some of the solid D-HPGA and 6-APA present dissolved such that the outlet from the feed tank contained saturated D-HPGM and 6-APA. When the total concentrations of D-HPCM and 6-APA came down to about 225 mM HPGM and 225 mM 6-APA, more solid substrate was added to the feed tank. At intervals the crystals in the centrifuge were washed with water, the washing liquid was added to the reactor. The amount of water used was sufficient to keep the volume in the reactor at its starting level. After washing the crystals in the centrifuge, the centrifuge was emptied.

After about 12 hours, the dosing of D-HPGM and 6-APA was stopped. After 14 hours, the 6-APA concentration reached 20 mM and the reaction was stopped. The amounts of reaction components are given in Table 1, below.

TABLE 1

|  | substrate added | crystal cake at the end | in solution at the end |
|---|---|---|---|
| D-HPGM | 606.5 g (3351 mmol) | 2.0 g (11 mmol) | 10.9 g (60 mmol) |
| 6-APA | 523.4 g (2423 mmol) | 9.0 g (42 mmol) | 4.3 g (20 mmol) |

TABLE 1-continued

|  | substrate added | crystal cake at the end | in solution at the end |
|---|---|---|---|
| Amoxicillin. 3H$_2$O | 0 | 909.6 g (2171 mmol) | 8.4 g (20 mmol) |
| D-HPG | 0 | 123.7 g (741 mmol) | 30.0 g (180 mmol) |

Based on the above results, the following yield can be calculated: amoxicillin yield (isolated product, based on 6-APA added): 90%.
Amoxicillin productivity: 156 mmol/hour/liter.

Hereinafter, the molar ratior between the amount of β-latam derivative which is formed and the amount of the acid form of the acylating agent formed has been designated R. In this example R=2.4.

A comparative experiment was performed at batchwise conditions and the reaction was stopped at the moment where the optimum yield of amoxicillin was obtained (2 hours). The reaction temperature was about 20° C., the pH value was about 6.1 and 26250 units of the enzyme, mentioned in this example above, was used. The total volume of the reaction mixture was 1 liter. The reaction was performed in the reactor mentioned above. After 2 hours the bottom valve was opened, and the crystals were separated from the immobilized enzyme particles by the bottom sieve in the reactor. The crystal suspension was filtered. The amounts of reaction components are given in Table 2, below.

TABLE 2

|  | substrate added | crystal cake at the end | in solution at the end |
|---|---|---|---|
| D-HPGM | 90.5 g (500 mmol) | 0.1 g (0.6 mmol) | 34.2 g (189 mmol) |
| 6-APA | 43.2 g (200 mmol) | 0.7 g (3 mmol) | 3.0 g (14 mmol) |
| Amoxicillin. 3H$_2$O | 0 | 70.8 g (169 mmol) | 4.2 g (10 mmol) |
| D-HPG | 0 | 0.3 g (2 mmol) | 21.7 g (130 mmol) |

Amoxicillin yield (isolated product, based on 6-APA added): 85%.
Amoxicillin productivity: 90 mmol/hour/liter.
R = 1.4.

EXAMPLE 2

Enzymatic Preparation of Amoxycillin from D-HPGA and 6-APA

The equipment for this experiment is described in example 1.

A mixture consisting of D-HPGA (20.0 g, 120 mmol) and 6-APA in 800 ml water, which was adjusted at a pH value of 6.0 by adding 4 M ammonium hydroxide, was added to the reactor with the bottom valve closed. The stirring was started. Immobilized Penicillin G acylase (26250 U, size 200–500 μm) made up to 200 ml was added to the reactor. The pH value was maintained at 6.0. The reaction temperature was about 20° C. Under these conditions the reaction mixture was almost saturated with D-HPGA and 6-APA. Then the bottom valve was opened allowing the reaction mixture from the reactor to enter the centrifuge. Thereafter, the mother liquor from the centrifuge was pumped into the feed tank wherein D-HPGA (20.0 g, 120 mmol) and 6-APA (20.0 g, 92.5 mmol) were loaded. The total volume of the suspension in the feed tank was kept at about 75 ml. A flow of about 100 ml/min was maintained in the system. The concentration of reaction components in the reactor, in the reactor outlet, in the centrifuge outlet, in the feed tank, and in the feed tank outlet were monitored by analytical HPLC.

The crystals formed in the reactor were separated from the immobilized enzyme particles by the bottom sieve in the reactor. The crystal suspension was led to the centrifuge where the crystals were separated from the mother liquor. The mother liquor was passed through the feed tank. When the total concentrations in the feed tank came down to about 150 mM HPGA and 225 mM 6-APA, more solid was added to the feed tank. At intervals the crystals in the centrifuge were washed with water, the washing liquid was added to the reactor. The amount of water used was sufficient to keep the volume in the reactor at its starting level. After washing the crystals in the centrifuge, the centrifuge was emptied.

After about 12 hours, the dosing of 6-APA to the feed tank was stopped while the D-HPGA dosing was maintained in order to keep D-HPGA at saturation. After 14 hours, the 6-APA concentration reached 20 mM and the reaction was stopped. The amounts of reaction components are given in Table 3, below.

TABLE 3

| | substrate added | crystal at the end | in solution at the end |
|---|---|---|---|
| D-HPGA | 483.9 g (2915 mmol) | 1.3 g (8 mmol) | 22.4 g (135 mmol) |
| 6-APA | 443.0 g (2051 mmol) | 8.0 g (37 mmol) | 4.3 g (20 mmol) |
| Amoxicillin. 3H$_2$O | 0 | 758.4 g (1810 mmol) | 8.4 g (20 mmol) |
| D-HPG | 0 | 103.2 g (618 mmol) | 29.7 g (178 mmol) |

Amoxicillin yield (isolated product, based on 6-APA added): 88%.
Amoxicillin productivity: 131 mmol/hour/liter.
R = 2.3.

We claim:

1. A process for preparing a β-lactam compound comprising catalyzing the acylation of an amino β-lactam with an acylating agent for at least 5 hours with an amidase or acyclase to produce said β-lactam compound and the acid form of the acylating agent, wherein the concentration of the amino β-lactam and the concentration of the acylating agent are both constantly higher than 70% of the lowest value of the saturated concentrations of the amino β-lactam and the acylating agent, respectively, and wherein the amino β-lactam compound is removed continuously or semicontinuously from the reaction mixture.

2. A process for preparing a β-lactam compound comprising catalyzing the acylation of an amino β-lactam with an acylating agent for at least 5 hours with an amidase or acyclase to produce said β-lactam compound and the acid form of the acylating agent, wherein the concentration of the amino β-lactam and the concentration of the acylating agent are both constantly higher than 70% of the lowest value of the saturated concentration of the amino β-lactam and the saturated concentration of the acylating agent, respectively, and wherein both the amino β-lactam and the acylating agent are added continuously or semicontinuously to the reaction mixture; and recovering the β-lactam compound.

3. The process according to claim 1, wherein said acid form of the acylating is removed continuously or semicontinuously from the reaction mixture.

4. The process according to claim 1, wherein the concentrations of the amino β-lactam and the acylating agent are both individually higher than 85% of the lowest value of the saturated concentrations of the amino β-lactam and the acylating agent, respectively.

5. The process according to claim 1, wherein for a period of about 5 hours, the ratio between the net rate of formation of said β-lactam compound in the reaction mixture and the rate of formation of said acid form of the acylating agent in the reaction mixture does not deviate more than about 50% from the average ratio between net rate of formation of said β-lactam compound and the total rate of formation of said acid form of said acylating agent during said period of 5 hours.

6. The process according to claim 5, wherein said ratio, for a period of about 10 hours, does not deviate more than about 50% from said average ratio.

7. The process according to claim 5, wherein said ratio does not deviate more than about 20% from said average ratio.

8. The process according to claim 7, wherein said ratio does not deviate more than about 10% from said average ratio.

9. The process according to claim 2, wherein said rate of formation, for a period of about 10 hours, does not deviate more than about 50% from said average rate of formation during the same period of time.

10. The process according to claim 2, wherein said rate of formation does not deviate more than about 20% from said average rate of formation.

11. The process according to claim 10, wherein said rate of formation does not deviate more than about 10% from said average rate of formation.

12. The process according to claim 1, wherein for a period of about 5 hours, the rate of formation of said β-lactam compound in the reaction mixture, does not deviate more than about ±50% from said average rate of formation of said β-lactam compound during said period of time.

13. The process according to claim 1, wherein the amount of dissolved and optionally precipitated β-lactam compound in the reaction mixture is present in a concentration which does not exceed 350 mMol/liter.

14. The process according to claim 1, wherein the amino β-lactam is selected from the group consisting of 6-aminopenicillanic acid, 7-aminodesacetoxycephalosporanic acid, 7-aminocephalosporanic acid, 7-amino-3-chloro-3-cephem-4-carboxylate and 7-amino-3-3-cephem-4-carboxylate.

15. The process according to claim 1, wherein the acylating agent is selected from the group consisting of an activated form of D phenylglycine, D p-hydroxyphenylglycine, D-2,5-dihydrophenylglycine and mandelic acid.

16. The process according claim 1, wherein the β-lactam compound is selected from the group consisting of ampicillin, amoxicillin, cefaclor, cephalexin, cephadroxil, cephradine, epicillin and cefamandol.

17. A process according to claim 1, wherein said process is performed at a temperature in the range from about 0 to about 35° C.

18. The process according to claim 1, wherein said process is performed at a temperature in the range from about 10 to about 35° C.

19. The process according to claim 1, wherein said process is performed at a pH value in the range from about 5 to about 8.

20. The process according to claim 1, wherein the amino β-lactam is prepared by hydrolysis of a compound selected from the group consisting of penicillin V, penicillin G, 7-phenoxyacetamidodesacetoxycephalosporanic acid, 7-phenylacetamidodesacetoxycephalosporanic acid and Cephalosporin C.

21. The process according to claim 1, wherein the acylating agent is an amide wherein the —COHN$_2$ is unsubstituted or an ester containing 1–3 carbon atoms in the alcohol part.

22. The process according to claim 1, wherein the amidase or acylase is used in a immobilized form.

23. The process according to claim 24, further comprising an organic solvent.

24. The process according to claim 1, which process is carried out in an aqueous solution.

25. The process according to claim 16, wherein the amidase or acylase used is selected from the group consisting of amidase or acylase derived from *Escherichia coli, Acetobacter pasteurianum, Xanthomonas citril, Kluyvera citrophilia, Bacillus mageterium* or *Alcaligenes faecalis.*

* * * * *